(12) United States Patent
Rathjen

(10) Patent No.: US 11,938,060 B2
(45) Date of Patent: *Mar. 26, 2024

(54) DEVICE FOR TREATING EYE TISSUE USING LASER PULSES

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/122,846

(22) Filed: Mar. 17, 2023

(65) Prior Publication Data

US 2023/0218442 A1 Jul. 13, 2023

Related U.S. Application Data

(63) Continuation of application No. 16/711,948, filed on Dec. 12, 2019, now Pat. No. 11,628,090, which is a (Continued)

(30) Foreign Application Priority Data

Apr. 29, 2013 (EP) ..................................... 13002266

(51) Int. Cl.
 *A61F 9/008* (2006.01)
 *A61F 9/009* (2006.01)
(52) U.S. Cl.
 CPC .... *A61F 9/008* (2013.01); *A61F 2009/00897* (2013.01); *A61F 9/009* (2013.01)

(58) Field of Classification Search
 CPC .................................. A61F 9/008; A61F 9/009
 See application file for complete search history.

(56) References Cited

U.S. PATENT DOCUMENTS

2005/0288745 A1* 12/2005 Andersen ............ A61F 9/00781
  607/86
2008/0015553 A1* 1/2008 Zacharias ............... A61F 9/008
  606/4

(Continued)

FOREIGN PATENT DOCUMENTS

JP 2000/338430 A 12/2000
WO 2002/32353 A2 4/2002

*Primary Examiner* — Allen Porter
*Assistant Examiner* — Skylar Lindsey Christianson
(74) *Attorney, Agent, or Firm* — Banner & Witcoff, Ltd.

(57) ABSTRACT

An ophthalmic device for treating eye tissue using laser pulses comprises a projection optical unit for focused projection of the laser pulses and a scanning device, with a movable mirror, arranged downstream from the projection optical unit, for deflecting the laser pulses projected by the projection optical unit in at least one deflection direction. The ophthalmic device moreover comprises an optical correction element arranged downstream of the scanning device, which correction element is configured to image, in a focused manner, the laser pulses deflected by the scanning device on an intended treatment area in the eye tissue. The optical correction element renders it possible to therefore correct image field curvatures caused by the scanning device arranged downstream from the projection optical unit and, for example, image the deflected laser pulses in focus onto a plane.

16 Claims, 5 Drawing Sheets

Related U.S. Application Data continuation of application No. 14/264,198, filed on Apr. 29, 2014, now Pat. No. 10,537,475.

(56) References Cited

U.S. PATENT DOCUMENTS

| | | | |
|---|---|---|---|
| 2009/0187174 A1* | 7/2009 | Rathjen | G02B 21/02 |
| | | | 606/5 |
| 2010/0067079 A1 | 3/2010 | Rathjen | |
| 2011/0196350 A1 | 8/2011 | Friedman et al. | |
| 2011/0245814 A1* | 10/2011 | Taboada | A61F 9/008 |
| | | | 606/4 |
| 2012/0078241 A1* | 3/2012 | Gooding | A61F 9/009 |
| | | | 606/6 |
| 2013/0144277 A1 | 6/2013 | Rathjen et al. | |
| 2014/0257256 A1* | 9/2014 | Hohla | A61F 9/008 |
| | | | 606/4 |

* cited by examiner

DEVICE FOR TREATING EYE TISSUE USING LASER PULSES

CROSS REFERENCE TO RELATED APPLICATIONS

The present application is a continuation application of U.S. application Ser. No. 16/711,948, filed Dec. 12, 2019, which is a continuation application of U.S. application Ser. No. 14/264,198, filed Apr. 29, 2014, now U.S. Pat. No. 10,537,475, which claims benefit of European Application No. 13002266.8, filed Apr. 29, 2013, the disclosures of which are each incorporated herein by reference in its entirety.

TECHNICAL FIELD

The present disclosure relates to an ophthalmic device for treating eye tissue using laser pulses. In particular, the present disclosure relates to an ophthalmic device for treating eye tissue using laser pulses, comprising a projection optical unit for focused projection of the laser pulses into the eye tissue and a scanning device arranged downstream from the projection optical unit, for deflecting the laser pulses projected by the projection optical unit in at least one deflection direction.

BACKGROUND

Ophthalmic devices for treating eye tissue using laser pulses, in which the scanning device is arranged downstream from the projection optical unit, are advantageous in that they have a simple focusing optical unit. However, a disadvantage thereof is that, as a result of the downstream connection of the scanning device, there is an image field curvature, i.e. a curved treatment surface. In order to compensate for this image field curvature, the focus of the laser pulses deflected by the scanning device needs to be corrected.

US 2011/245814 describes a device with a downstream scanning device with a single mirror suspended by means of a universal joint, which enables short work distances and strong focusing, as are of interest in e.g. ophthalmology for lens surgery. However, a disadvantage of this arrangement lies in the restricted dynamic response as a result of co-rotating drives. Moreover, the mirror surface in accordance with US 2011/245814 does not lie in the center of the rotation, leading to an additional distortion of the image field curvature because the mirror is displaced along the optical axis during scanning.

SUMMARY

Aspects of the present disclosure propose an ophthalmic device for treating eye tissue using laser pulses, which has a projection optical unit with a downstream scanning device and does not have at least some of the disadvantages of the known systems.

According to aspects of the present disclosure, these are achieved by the features of the independent claims. Moreover, further examples emerge from the dependent claims and the description.

The ophthalmic device for treating eye tissue using laser pulses comprises a projection optical unit for focused projection of the laser pulses and a scanning device, with a movable mirror, arranged downstream from the projection optical unit, for deflecting the laser pulses by the projection optical unit in at least one deflection direction.

In particular, the present disclosure describes the ophthalmic device moreover comprising an optical correction element arranged downstream of the scanning device, which correction element is configured to image, in a focused manner, the laser pulses deflected by the scanning device on an intended treatment area in the eye tissue.

In some examples, the optical correction element is configured to image, in a focused manner, the laser pulses deflected by the scanning device on a plane for correcting image field curvatures caused by the scanning device.

In some examples, the scanning device is configured to move the mirror about a pivot point lying on the optical axis of the projection optical unit and on the mirror surface.

In some examples, the scanning device comprises a plurality of linear drives coupled to the mirror and the ophthalmic device comprises a control module configured to control the linear drives in such a way that the linear drives rotate the mirror about a pivot point lying on the optical axis of the projection optical unit and on the mirror surface.

In some examples, the optical correction element is an example as a lens element.

In some examples, the lens element has a lens surface equidistant to the pivot point of the mirror.

In some examples, the scanning device is configured to move the mirror about a pivot point lying away from the optical axis of the projection optical unit and the optical correction element is embodied as an anamorphic optical element.

In some examples, the ophthalmic device comprises a patient interface device which can be fastened to the eye of the patient and which is rotatably mounted about the pivot point of the mirror.

In some examples, the ophthalmic device comprises a zoom system for adjusting a depth of focus in the projection direction, and a patient interface device which can be fastened to the eye of the patient and which is rotatably mounted about the optical axis of the zoom system.

In some examples, the optical correction element is securely or detachably connected to the patient interface device.

In some examples, the scanning device is embodied such that it can be moved out of the beam path between scanning device and eye in the state of the patient interface device in which it is fastened to the eye.

In some examples, the patient interface device has a cavity provided for holding liquid, and an opening, which opening is closed by the eye in the state of the patient interface device in which it is fastened to the eye.

In some examples, the projection optical unit has a diameter, which substantially corresponds to the largest extent of the mirror surface of the mirror.

In some examples, the optical correction element is embodied as lens element configured to image, in a focused manner, the laser pulses deflected by the scanning device on an intended treatment area away from the focal length of the projection optical unit.

In some examples, the ophthalmic device comprises a divergence modulator which is arranged upstream of the projection optical unit and configured to shift the divergence of the laser beam, depending on the deflection of the laser pulses, in such a way that image field curvatures caused by the scanning device are at least partly compensated.

In some examples, the divergence modulator comprises two optical lenses arranged in series, wherein at least one of the lenses is coupled to a movement driver in a manner displaceable on an optical axis for modulating the divergence of the laser beam; a deformable lens; a deformable mirror element; a spatial light modulator for modulating the wavefront of the laser beam; an area light modulator for modulating the reflection angles at a plurality of points of a reflection surface; a refraction modulator for modulating the refractive index of an optical element at a plurality of points in the cross section of the beam path; and/or an amplitude modulator for modulating the amplitude at a plurality of points in the cross section of the beam path of the laser beam.

In some examples, the ophthalmic device comprises a detection module configured to detect the optical correction element and control a setting of the scanning device depending on a detection of the optical correction element.

BRIEF DESCRIPTION OF THE DRAWINGS

In the following text, examples of the present disclosure are described on the basis of examples. The exemplary examples are illustrated by the following attached figures.

DETAILED DESCRIPTION

Figure 1:
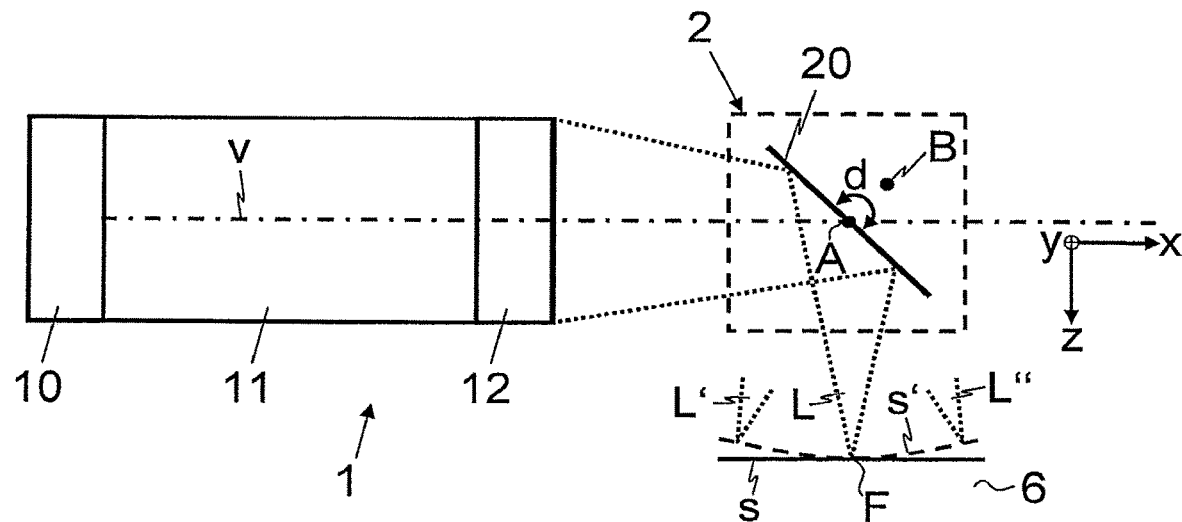
FIG. 1 schematically shows a cross section of an ophthalmic device for treating eye tissue using laser pulses, comprising a scanning device arranged downstream from the projection optical unit in accordance with one or more aspects of the present disclosure.

In FIGS. 1-10, reference sign 1 in each case relates to an ophthalmic device for treating eye tissue 6 using laser pulses.

The ophthalmic device 1 comprises a laser source 10 for producing the laser pulses, preferably femtosecond laser pulses, for treating eye tissue 6, and a projection optical unit 12 for the focused projection of the laser pulses. The laser pulses are supplied to the projection optical unit 12 from the laser source 10 by means of an optical transmission system 11.

As depicted schematically in FIGS. 1-10, the ophthalmic device 1 comprises a scanning device 2 arranged downstream from the projection optical unit 12. The scanning device 2 comprises at least one movable mirror 20 for deflecting the laser pulses projected by the projection optical unit 12 in at least one deflection direction by rotating d the mirror 20 around at least one axis of rotation. The scanning device 2 is preferably configured to move the mirror 20 around a plurality of axes of rotation which extend through a pivot point A lying on the optical axis v of the projection optical unit 12. As will be described later, the pivot point A is displaceable on the optical axis v. In other examples, the mirror 20 is rotatable around one or more axes of rotation which extend through a pivot point B lying outside of the optical axis v.

As depicted schematically in FIGS. 2, 3, 5, 6, the scanning device 2 comprises a drive system with a plurality of linear drives 21, 22 coupled to the mirror 20. By way of example, the drives are embodied as piezoelectric or electromagnetic drives. The ophthalmic device comprises a control module 23 configured to control the linear drives 21, 22 in such a way that these rotate the mirror 20 around a pivot point A, which preferably lies on the optical axis v of the projection optical unit 12 and on the mirroring surface of the mirror 20 (mirror surface), by translational movements u, w in correspondingly opposite directions. There being more than two linear drives 21, 22 enables rotations d around different axes extending through the pivot point A in the xyz-space.

As illustrated in FIG. 1, the rotation d of the mirror 20 of the downstream scanning device 2 causes curvature of the image field or an intended treatment surface s. In other words, the focus F of the laser beam L focused by the projection optical unit 12 moves on a circular arc s' in the case of a rotation d of the mirror 20 around an axis of rotation extending perpendicular to the plane of the drawing, or it moves on a spherical shell, as indicated in FIG. 1 by the deflected laser beams L', L", in the case of a rotation d of the mirror around a plurality of axes of rotation extending through a pivot point A lying on the optical axis v, wherein the circular arc s' or the spherical shell corresponds to the curved or distorted image field. A rotation around a pivot point B arranged outside of the optical axis v causes an additional distortion of the image field curvature, as is depicted, for example, in FIG. 5 by the circular arc s", since the mirror 20 is moreover displaced along the optical axis v by the rotational movement.

Figure 2:
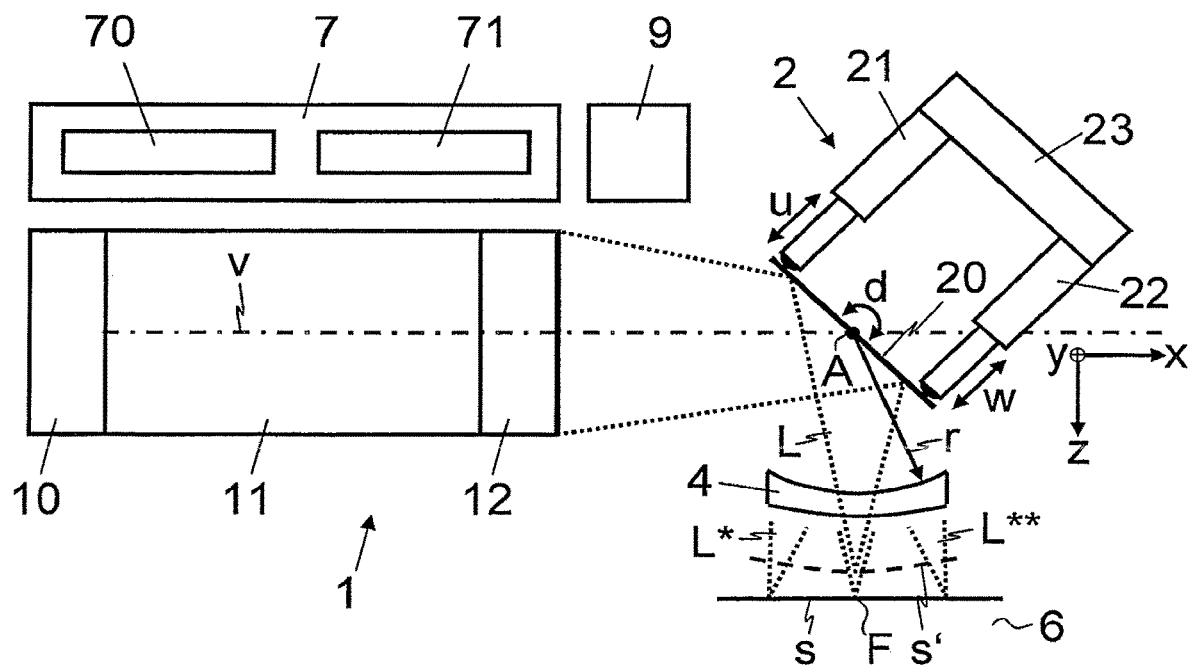
FIG. 2 schematically shows a cross section of an ophthalmic device for treating eye tissue using laser pulses, comprising a scanning device arranged downstream from the projection optical unit and an optical correction element arranged downstream from the scanning device in accordance with one or more aspects of the present disclosure.
Figure 3:
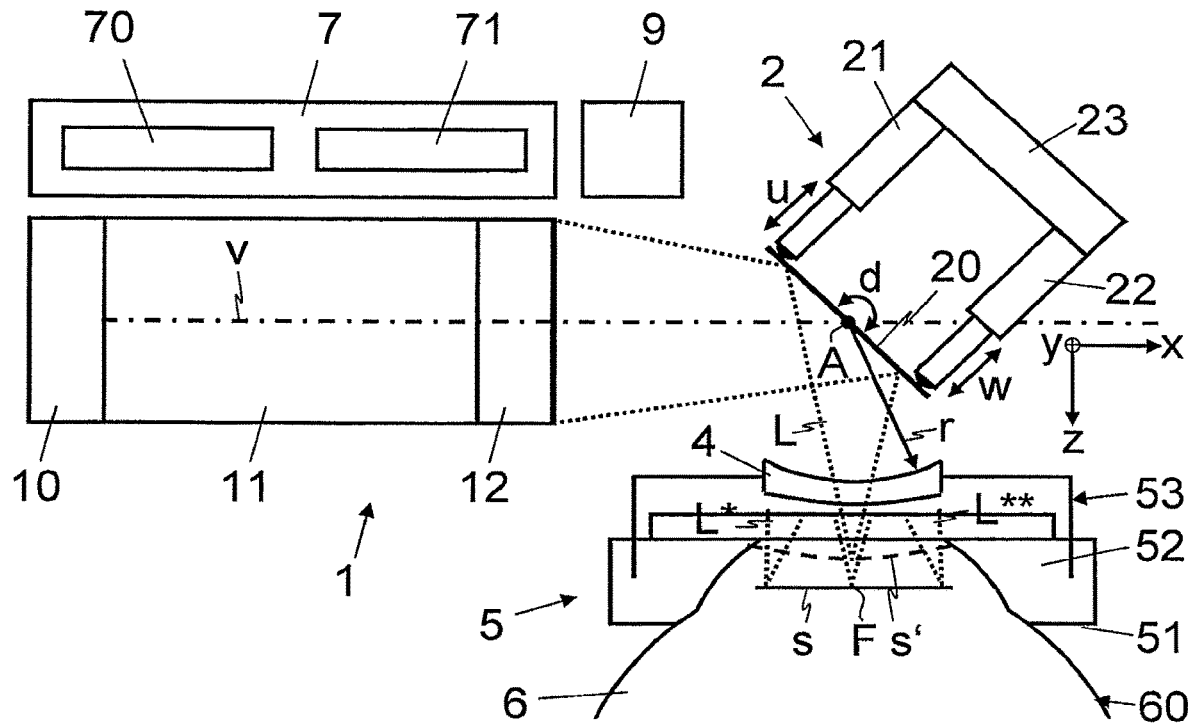
FIG. 3 schematically shows a cross section of an ophthalmic device for treating eye tissue using laser pulses, comprising a scanning device arranged downstream from the projection optical unit and an optical correction element arranged downstream from the scanning device and integrated into a patient interface in accordance with one or more aspects of the present disclosure.

In the examples illustrated in FIGS. 2 and 3, the ophthalmic device 1 comprises an optical correction element 4 arranged downstream from the scanning device 2, which correction element is configured to image the laser pulses deflected by the scanning device 2 in focus onto an intended treatment surface s in the eye tissue 6, for example onto an intended treatment plane for producing a planar cut, as indicated in FIG. 2 by the corrected laser beams L*, L**. In one variant, the correction element 4 is embodied as an optical lens element. By way of example, the lens element has a lens surface equidistant from the pivot point A of the mirror 20, as indicated in FIG. 2 by the radius r.

In order to increase the distance between the scanning device 2 and the eye of the patient, the optical correction element 4 is embodied as a lens element in some examples, which lens element is configured in such a way that the laser pulses deflected by the scanning device 2 are imaged in focus onto an intended treatment surface lying outside of the focal length f of the projection optical unit 12. That is to say, the lens element of the optical correction element 4 causes a defined displacement or enlargement of the focal length f of the projection optical unit 12. In a further example, the correction element 4 is additionally configured to increase the refractive power and therefore focus the laser beam more, i.e., project the laser beam onto a focus with a reduced spot size. The projection optical unit 12 and the optical correction element 4 are matched to one another in a targeted manner in one variant, in order, as a combined projection optical unit, to achieve a defined spot quality of the projected laser pulse or laser beam, for example in respect of size and shape (diameter across the projection direction, length in the projection direction).

Figure 5:
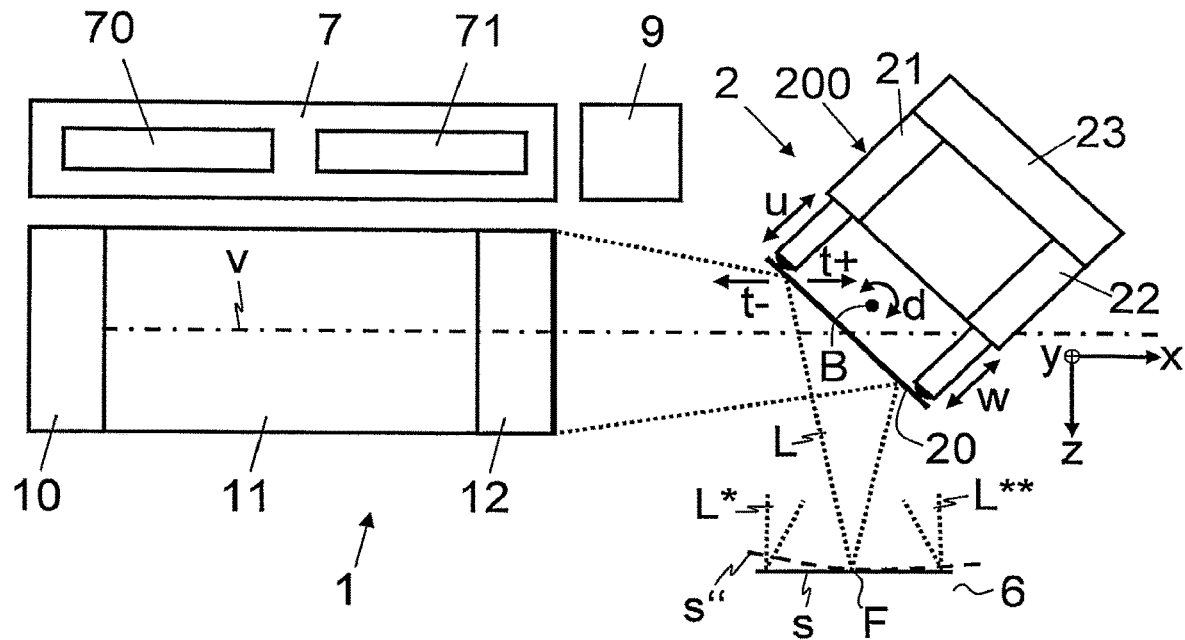
FIG. 5 schematically shows a cross section of an ophthalmic device for treating eye tissue using laser pulses, comprising a scanning device arranged downstream from the projection optical unit and a drive system for parallel displacement of a mirror of the scanning device, which mirror can be rotated around a pivot point arranged at a distance from the optical axis of the projection optical unit in accordance with one or more aspects of the present disclosure.

For configurations and/or applications in which the mirror 20 is rotated around a pivot point B lying outside of the optical axis v of the projection optical unit 12, use is made of a correction element 4 embodied as an anamorphic element since, when the deflection mirror of the scanning device 2 rotates around a pivot point B lying outside of the optical axis v of the projection optical unit 12, further distortions of the image field emerge, which distortions are characterized by asymmetry in respect of the projection axis (see e.g. circular arc s" around pivot point B in FIG. 5).

In other examples, the optical correction element 4 is securely or interchangeably connected to the ophthalmic device 1 or a patient interface device 5 of the ophthalmic device 1. Therefore, it is possible to insert different correction elements 4 into the patient interface device 5 in an interchangeable manner and use these for the treatment of the eye tissue 6.

As illustrated schematically in FIG. 3, the patient interface device 5 comprises, for example, a vacuum applicator 51, e.g. a suction ring, to be fastened to the eye 60 of the patient. In some examples, the patient interface device 5 comprises a contact body 52, e.g. an applanation body, for establishing contact on the cornea of the eye 60, or a cavity that can be filled with liquid, which cavity has an opening which is sealed by the eye 60 or the cornea in the state where the patient interface device 5 is applied to the eye 60. In some examples, the optical correction element 4 is configured as a contact body, either as an applanation body with a flat contact surface or as a contact body with a curved contact surface, depending on the variant and/or application. In some examples, the optical correction element 4 and a separate applanation body form an optical correction system configured to image the laser pulses deflected by the scanning device 2 in focus onto the intended treatment surface s in the eye tissue 6.

The patient interface device 5 is connected to the ophthalmic device 1 in some examples. For an ergonomic improvement of the applicability on the eye 60, the patient interface device 5 is rotatably mounted, for example around two axes of rotation. In some examples, the patient interface device 5 is rotatably mounted around the pivot point A of the mirror 20, i.e. the axes of rotation of the rotary joints of the patient interface device 5 extend through the pivot point A of the mirror 20. By way of example, one of the axes of rotation of the rotary joints of the patient interface device 5 corresponds to the optical axis v of the projection optical unit 12 or of a zoom system 83, described below, such that the patient interface device 5 is rotatable around the optical axis v (and, if the pivot point A of the mirror 20 lies on the optical axis v, also around this pivot point A).

In some examples, the scanning device 2 is embodied and connected to the ophthalmic device 1 in such a way that it can be moved out of the beam path by means of a repositioning device, for example by means of a rotation around a rotary joint or by means of a translation, such that it is possible to see into the eye 60. To this end, the repositioning device comprises a pivot bearing attached to the ophthalmic device 1 or a guide, by means of which pivot bearing or guide the scanning device 2 can be moved out of the beam path and can be coupled back into the beam path, either manually or by means of a drive system, such that, in the state where the scanning device 2 is coupled into the beam path, the laser pulses supplied by the projection optical unit 12 can again be deflected precisely onto target points F by the mirror 20 of the scanning device 2. It should be noted here that in the state in which the scanning device 2 is moved out of the beam path, an unhindered view of the eye 60 is possible, both in the state where the patient interface device 5 is fastened to the eye 60 and when the patient interface device 5 is not attached to the eye 60 or does not contact the eye 60, but is merely arranged over the eye 60.

In some examples, the ophthalmic device 1 comprises a detection module 9 configured to detect the optical correction element 4 and comprising a control module configured to control the setting of the scanning device 2 in respect of the position or the rotational angle of the mirror 20 depending on a detection of the optical correction element 4. The detection of the optical correction element 4 includes the position of the correction element 4 in respect of the ophthalmic device 1 or the scanning device 2, the type of correction element 4, optical properties of the correction element 4, which are e.g. assigned to the type of correction element 4, and/or dimensions of the correction element 4, in particular the thickness of the correction element 4. Depending the example and the parameters to be detected, the detection module 9 comprises one or more optical sensors, distance sensors, electrical sensors, electromechanical sensors and/or electromagnetic sensors, e.g., RFID sensors, for detecting the optical correction element 4. In particular, the control module of the detection module 9 is configured to control the scanning device 2 depending on the detected position of the correction element 4 and thereby dynamically adapt the position or the rotational angle of the mirror 20 to positional changes of the correction element 4 or of the patient in order to deflect the laser pulses to defined target points F in the eye tissue 6 depending on the position or positional changes. Moreover, the control module of the detection module 9 is configured to align the pivot point A of the mirror 20 with respect to the patient interface device 5 and to compensate the tile of the patient interface device 5 caused by rotary joints of the patient interface device 5.

Figure 4:
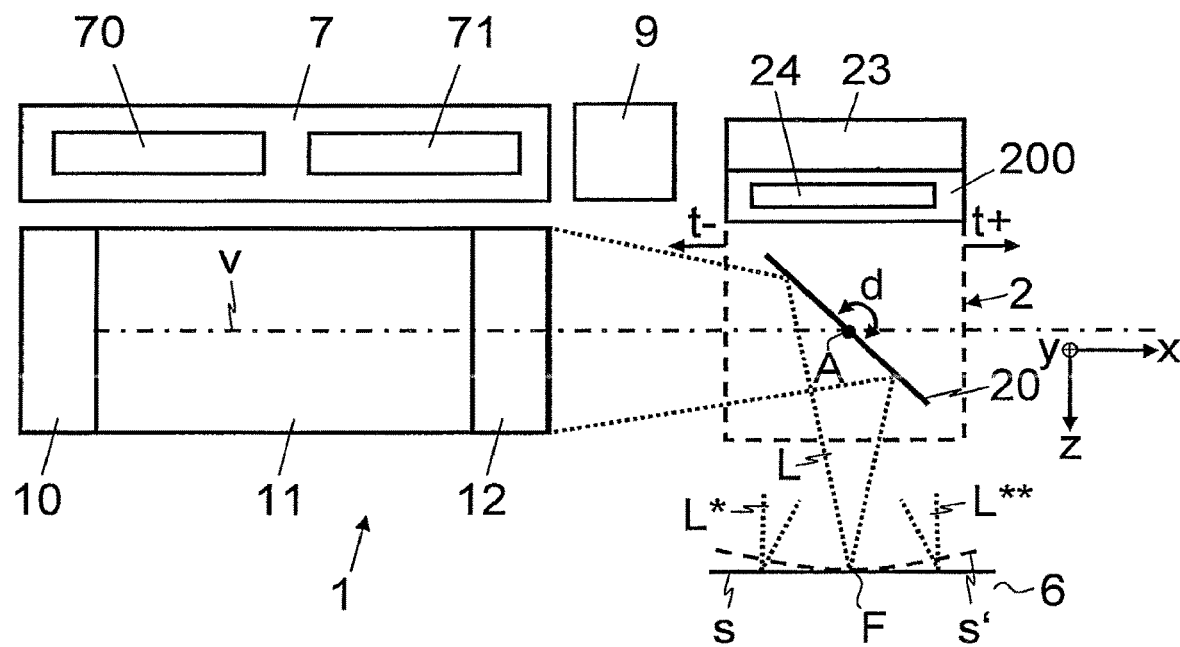
FIG. 4 schematically shows a cross section of an ophthalmic device for treating eye tissue using laser pulses, comprising a scanning device arranged downstream from the projection optical unit and a drive system for moving the scanning device in accordance with one or more aspects of the present disclosure.
Figure 6:
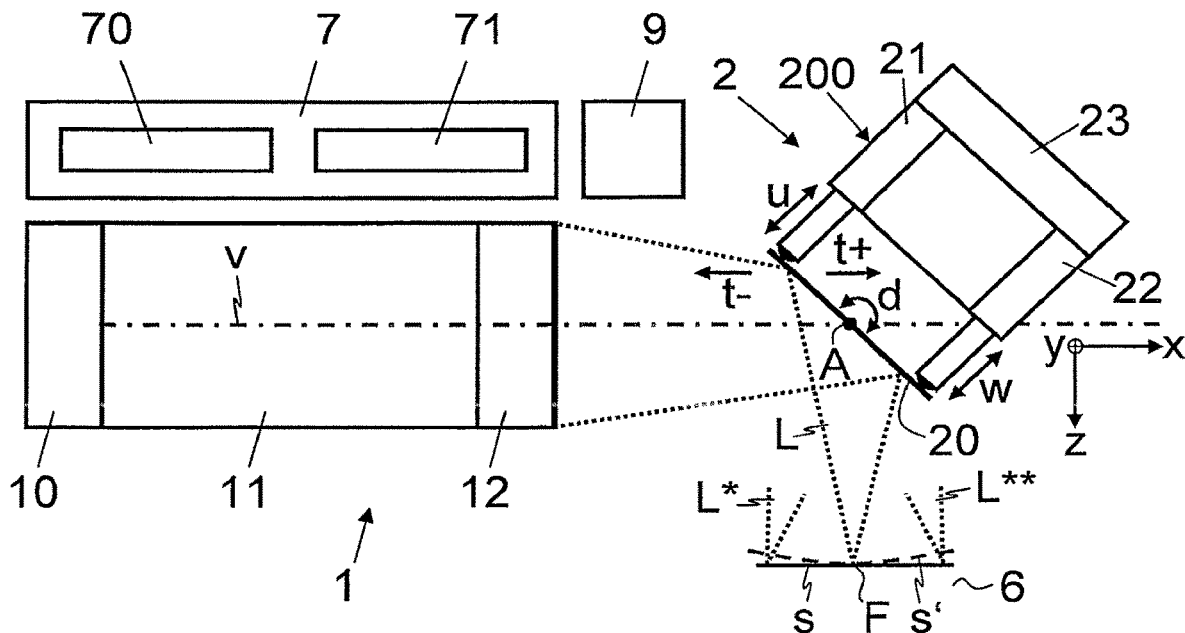
FIG. 6 schematically shows a cross section of an ophthalmic device for treating eye tissue using laser pulses, comprising a scanning device arranged downstream from the projection optical unit and a drive system for parallel displacement of a mirror of the scanning device, which mirror can be rotated around a pivot point arranged on the optical axis of the projection optical unit in accordance with one or more aspects of the present disclosure.

In the examples depicted in FIGS. 4, 5, and 6, the ophthalmic device 1 has a drive system 200 configured to displace the mirror 20 in parallel. In particular, the drive system 200 is configured to displace the mirror 20 with a translational movement component t−, t+ along the optical axis v. As a result of the parallel displacement of the mirror 20 of the scanning device 2 arranged downstream from the projection optical unit 12, the distance between the mirror surface and the projection optical unit 12 is modified, causing a shift in the focus in the projection direction in the case of an unchanged focal length f of the projection optical unit 12. Reducing the distance between the mirror surface and the projection optical unit 12 causes an increase in the distance between the focus and the mirror surface, and therefore enables a focused projection of the laser pulses onto lower lying points F in the eye tissue 6 (displacement in projection direction or z-direction); increasing the distance between the mirror surface and the projection optical unit 12 by contrast causes a reduction in the distance between the focus and the mirror surface, and therefore enables a focused projection of the laser pulses onto higher lying target points F in the eye tissue 6 (displacement counter to the projection direction or z-direction).

In the example according to FIG. 4, the direct system 200 for parallel displacement of the mirror 20 comprises a drive 24 coupled to the scanning device 2, which drive is configured to displace the scanning device 2 along the optical axis v of the projection optical unit 12 or across the optical axis v of the projection optical unit 12.

In the examples in FIGS. 5 and 6, the drive system 200 comprises at least one drive 21, 22 coupled to the mirror 20, which drive is configured to displace the mirror 20 in parallel. By way of example, the drive system 200 comprises a plurality of linear drives 21, 22 coupled to the mirror 20, which drives are configured to displace the mirror 20 in parallel.

As depicted schematically in FIGS. 5 and 6, the linear drives 21, 22 are moreover configured to rotate the mirror 20 around at least one pivot point A, B by means of correspondingly opposing translational movements u, w. In the illustration of FIG. 5, the rotation d is performed around a pivot point B lying outside of the optical axis v of the projection optical unit 12. In the illustration of FIG. 6, the rotation d is performed around a pivot point A lying on the optical axis v of the projection optical unit 12 and on the mirror surface of the mirror 20. There being more than two linear drives 21, 22 enables rotations d around different axes extending through the pivot point A, B in the xyz-space. Therefore, the drive system 200 allows the mirror 20 and the pivot point A, B thereof to be displaced along the optical axis v of the projection optical unit 12 and the mirror 20 to be rotated around the pivot point A, B in order to treat the eye tissue 6 by means of laser pulses deflected in focus onto target points F.

Figure 7:
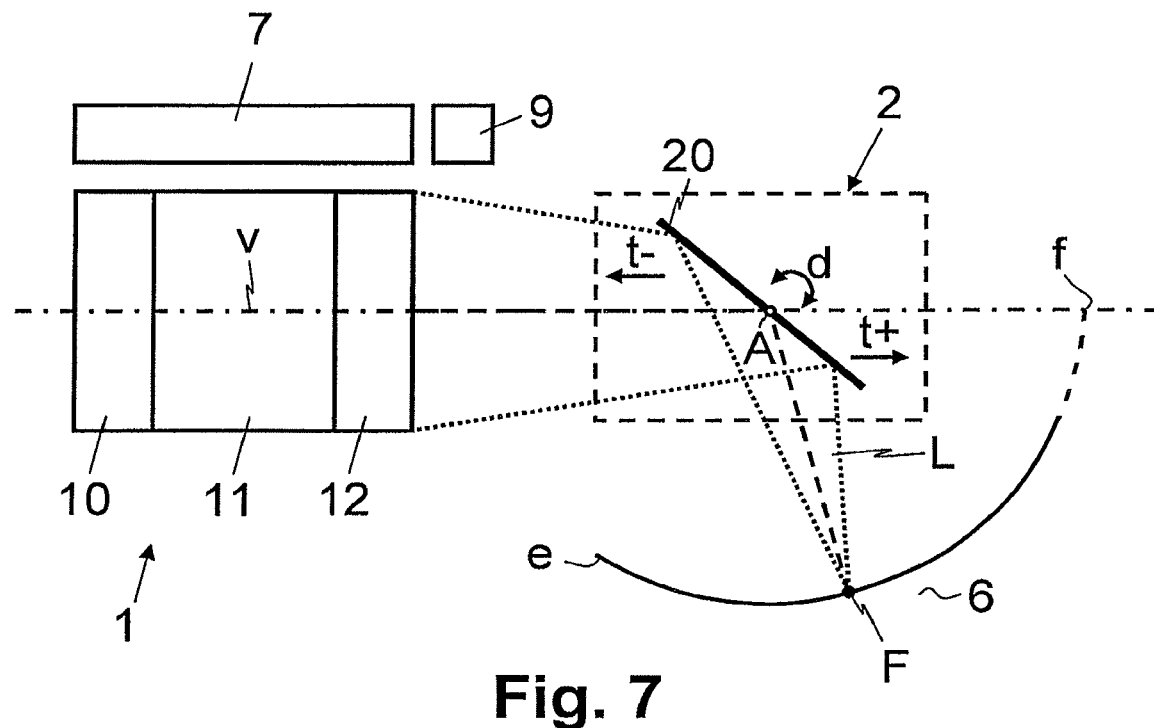
FIG. 7 schematically illustrates the deflection of a laser pulse onto a target point in the eye tissue by rotating the mirror of the scanning device arranged downstream from the projection optical unit in accordance with one or more aspects of the present disclosure.

FIG. 7 schematically illustrates the focal length f of projection optical unit 12 on the optical axis v and the circular arc e defined thereby, on which the deflected laser beam L can be deflected in focus in the case of a rotation d of the mirror 20 around an axis of rotation extending through the pivot point A normally to the plane of the drawing, or the spherical shell defined by the focal length, on which spherical shell the deflected laser beam L can be deflected in focus in the case of rotations d of the mirror 20 around a plurality of axes of rotation extending through the pivot point A.

Figure 8:
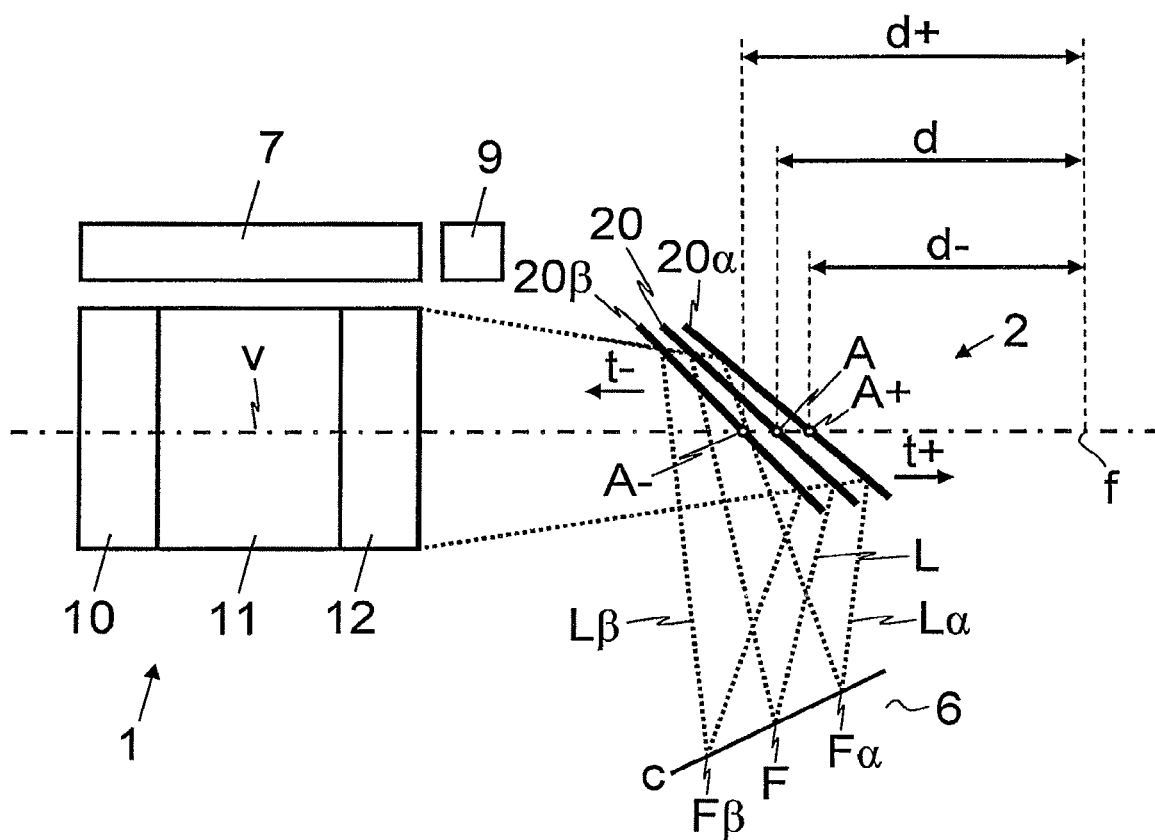
FIG. 8 schematically illustrates the scanning of target points on a treatment surface in the eye tissue by parallel displacement and rotation of the mirror of the scanning device arranged downstream from the projection optical unit in accordance with one or more aspects of the present disclosure.

FIG. 8 schematically illustrates the combination of a rotation d of the mirror 20 around the pivot point A, lying on the optical axis v and on the mirror surface, with a movement of the mirror 20 or of the pivot point A with a translational movement component t−, t+ along the optical axis v. FIG. 8 illustrates the combination of rotation d and displacement of the mirror 20 using the example of treating target points Fα, F, Fβ lying on a treatment line c in the eye tissue 6. As shown in FIG. 8, the control module 23 controls the drive system 200 or the linear drives 21, 22 in such a way that, for treating the target points Fα, F, Fβ, the drive system 200 displaces the pivot point or the mirror 20 to a point A−, A, A+ on the optical axis v of the projection optical unit 12, which point has a defined distance d−, d, d+ with respect to the focal length f of the projection optical unit 12. The pivot point A−, A, A+ therefore lies on a point of intersection between the mirror surface and the optical axis v, wherein the distance d−, d, d+ from the pivot point A−, A, A+ or from the point of intersection with respect to the focal length f of the projection optical unit 12 corresponds to the distance between the relevant target point Fα, F, Fβ and the pivot point A−, A, A+ or point of intersection. The focal length f of the projection optical unit 12 and the relevant target point Fα, F, Fβ therefore each lie on a common circular arc e or on a common spherical shell around the pivot point A−, A, A+ or point of intersection on the optical axis v. Here, the mirror 20 is rotated around the pivot point A−, A, A+ in such a way that the deflected mirror 20a, 20, 2013 deflects the laser beam Lα, L, Lβ in the direction of the target point Fa, F, FP. Hence the laser beam Lα, L, Lβ or the laser pulses is/are projected in focus onto the relevant target point Fα, F, Fβ on the treatment line c by the projection optical unit 12 by means of the deflected mirror 20α, 20, 20β. It should be noted here that the combination of rotation d and displacement should not be performed sequentially but preferably in parallel/simultaneously such that the target points Fα, F, Fβ can be put into focus and treated as quickly as possible.

In one variant, the control module 23 is configured to control the drive system 200 and the scanning device 2 in such a way that the laser pulses are deflected in focus and projected onto target points Fα, F, Fβ of a three-dimensional treatment surface s in the eye tissue 6. Three-dimensional treatment or volume treatment is achieved thereby.

In the following paragraphs and with reference to FIGS. 9 and 10, some examples of the ophthalmic device 1 with a correction system are described, which correction system is configured to undertake a change in focal length depending on the deflection of the laser pulses by means of one or more optical elements arranged upstream from the projection optical unit 12 or integrated into the projection optical unit 12.

Figure 9:
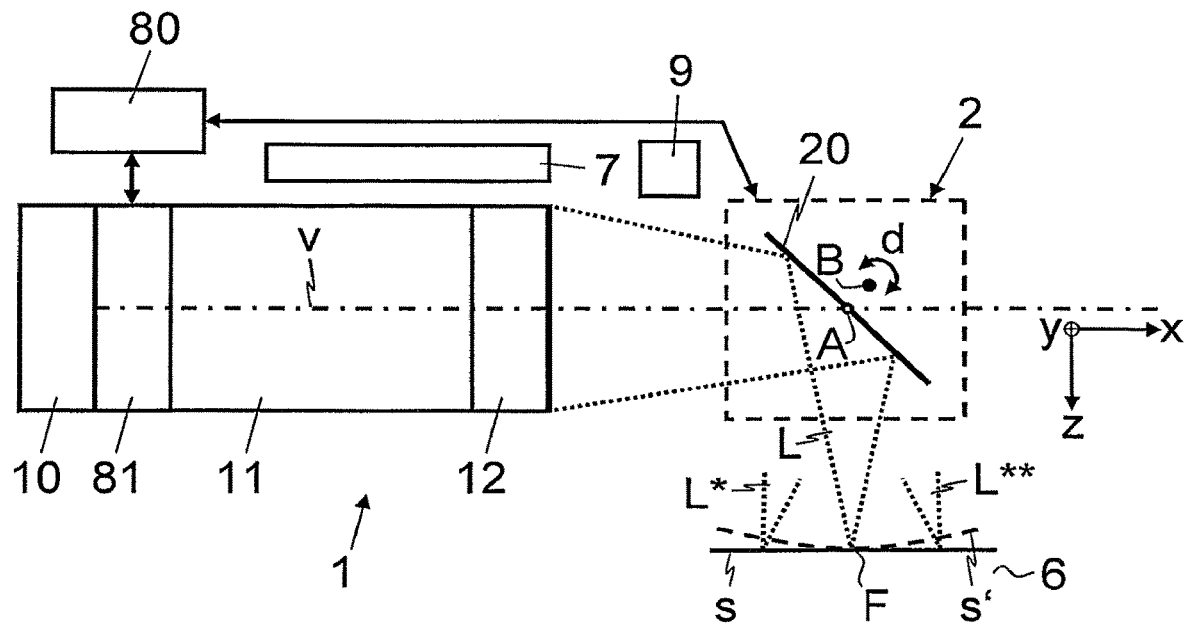
FIG. 9 schematically shows a cross section of an ophthalmic device for treating eye tissue using laser pulses, comprising a scanning device arranged downstream from the projection optical unit and a correction system for a change in focal length depending on the deflection of the laser pulses in accordance with one or more aspects of the present disclosure.

FIG. 9 illustrates an example in which the ophthalmic device 1 has a divergence modulator 81, arranged upstream from the projection optical unit 12, as a further feature in the optical transmission system 11. The divergence modulator 81 is configured to shift the divergence of the laser beam depending on the deflection of the laser pulses in such a way that image field curvatures caused by the scanning device 2 are compensated for, at least in part. Depending on the example, the divergence modulator 81, for divergence modulation, comprises two optical lenses arranged in series, wherein at least one of the lenses is coupled to a movement driver in a manner displaceable on the optical axis v for modulating the divergence of the laser beam; a deformable lens; a deformable mirror element; a spatial light modulator for modulating the wavefront of the laser beam; an area light modulator for modulating the reflection angles at a plurality of points of a reflection surface; a refraction modulator for modulating the refractive index of an optical element at a plurality of points in the cross section of the beam path; and/or an amplitude modulator for modulating the amplitude at a plurality of points in the cross section of the beam path of the laser beam. The divergence modulator 81 is controlled by a control module 80 depending on the deflection of the laser pulses performed by the scanning device 2, i.e. depending on one more deflection angles of one or more mirrors 20 of the scanning device 2. To this end, the control module 80 uses correction parameters or control values for controlling the divergence modulator 81, which correction parameters or control values are stored in a manner assigned to various deflection angles and cause a corresponding divergence modulation for compensating image field curvatures at the respectively relevant deflection angle, as indicated in FIG. 9 by the corrected laser beams L*, L**.

Figure 10:
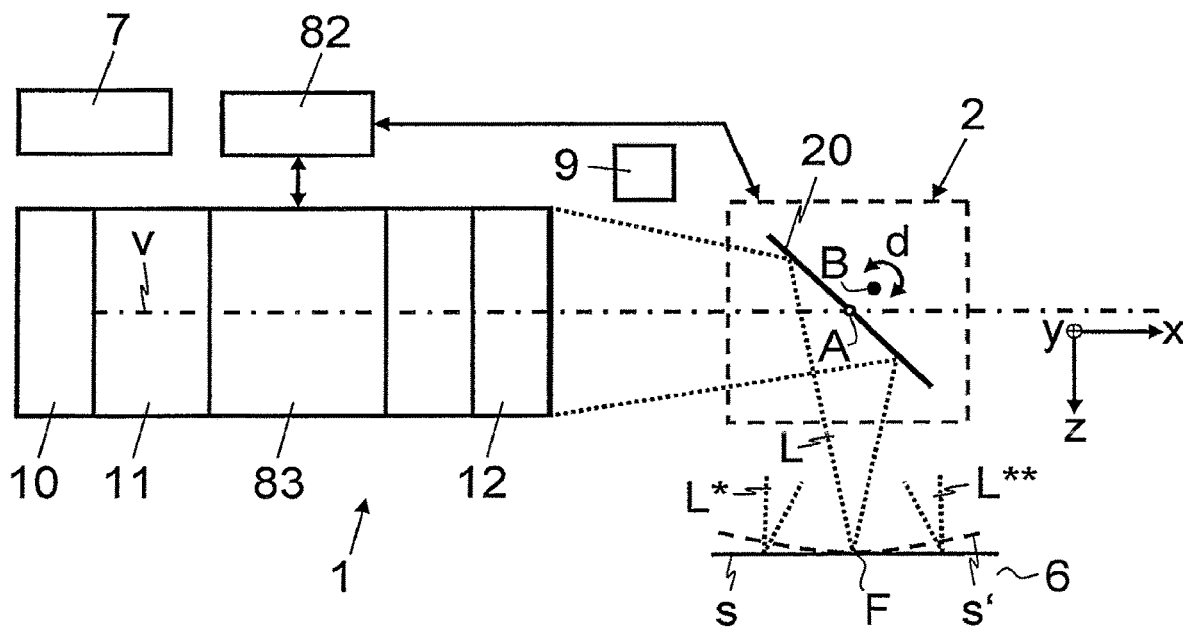
FIG. 10 schematically shows a cross section of an ophthalmic device for treating eye tissue using laser pulses, comprising a scanning device arranged downstream from the projection optical unit and a zoom system for a change in focal length depending on the deflection of the laser pulses in accordance with one or more aspects of the present disclosure.

FIG. 10 illustrates an example, in which the ophthalmic device 1 has a zoom system 83, arranged upstream from the projection optical unit 12 or integrated into the projection optical unit 12, as a further feature in the optical transmission system 11. The zoom system 83 is configured to undertake a change in focal length depending on the deflection of the laser pulses in order to compensate, at last in part, image field curvatures caused by the scanning device 2. The zoom system 83 is moreover configured to set the spot size and/or aberrations. The zoom system 83 comprises at least two optical systems that can be set individually, for example two lens groups, each with one or more movable lenses, and/or one or more deformable mirrors/lenses and correction elements that can be inserted. The optical systems are coupled to a drive system comprising one or more electric motors and configured to set the optical systems individually, for example, by displacing lenses along the optical axis v and/or normally to the optical axis v (into/out of the beam path). The zoom system 83 is controlled by a control module 82, depending on the deflection of the laser pulses performed by the scanning device 2, i.e. depending on one or more deflection angles of one or more mirrors 20 of the scanning device 2. To this end, the control module 82 uses correction parameters or control values for controlling the zoom system 83, which correction parameters or control values are stored in a manner assigned to various deflection angles and cause a corresponding change in focal length for compensating image field curvatures at the respectively relevant deflection angle, as indicated in FIG. 10 by the corrected laser beams L*, L**.

In different examples, the projection optical unit 12 is embodied as a zoom system 83 or the zoom system 83 is used as a projection optical unit 12. In some examples, the whole projection optical unit 12 is displaced depending on the deflection of the laser pulses so as to cause a compensating focus shift. In some examples, provision is made for a divergence modulator 81 and a zoom system 83, which are actuated in such a way that they undertake a shift in focus, depending on the deflection of the laser pulses, by a combination of a divergence modulation of the laser beam by means of the divergence modulator 81 and a focal length change by means of the zoom system 83.

In some examples, the ophthalmic device 1 comprises a compensation system 7 comprising movable masses 70 for compensating for acceleration forces caused by moved optical elements in order to avoid vibrations of the ophthalmic device 1 where possible or at least to reduce these. The compensation system 7 comprises one or more drives 71 coupled to the masses 70 and configured to move the masses 70 against the movements of the optical elements in accordance with the control by a control module. By way of example, the masses 70 are configured to compensate acceleration forces which are caused by the movements of optical elements of the scanning device 2, for example by movements of the mirror 20 and/or of the drives 21, 22, of the divergence modulator 81 and/or of the zoom system 83.

It should be noted here that the control modules 23, 80, 82, which were listed and described in the preceding paragraphs, each comprise a circuit, for example a (micro) processor, which is controlled by computer code of a program stored on a (non-transient) computer-readable medium, or another programmed logic unit or control electronics. The control modules 23, 80, 82 generate control signals, for example depending on control programs and/or feedback signals of the scanning device 2, of the divergence modulator 81 or of the zoom system 83, for controlling the scanning device 2, the drive system 200, the linear drives 21, 22, the divergence modulator 81, the zoom system 83, and/or the compensation system 7.

What is claimed is:

1. An ophthalmic device for treating eye tissue using laser pulses, comprising:
    a laser source configured to produce the laser pulses;
    an optical focusing unit configured to focus the laser pulses;
    a scanning device, with a movable mirror, arranged downstream from the optical focusing unit, and configured to deflect the laser pulses from the optical focusing unit in at least one deflection direction, whereby moving the mirror causes an image field curvature; and
    an optical correction element arranged downstream of the scanning device and configured to correct the image field curvature, by imaging, in a focused manner, the laser pulses deflected by the scanning device on an intended treatment area in the eye tissue
    wherein the optical focusing unit has a focal length; and
    the optical correction element comprises a lens configured to produce a defined displacement or enlargement of the focal length of the optical focusing unit.

2. The ophthalmic device of claim 1, wherein the movable mirror has a pivot point; and the lens element has a lens surface equidistant to the pivot point of the mirror.

3. The ophthalmic device of claim 1, wherein the optical focusing unit comprises one or more lenses configured to focus the laser pulses to a focal point in the eye tissue.

4. The ophthalmic device of claim 1, wherein the optical correction element comprises an anamorphic optical element.

5. The ophthalmic device of claim 1, wherein the optical focusing unit has an optical axis; the scanning device is configured to move the mirror about a pivot point lying away from the optical axis of the optical focusing unit; and the optical correction element comprises an anamorphic optical element.

6. The ophthalmic device of claim 1, wherein the optical correction element is configured as a contact body, whereby the contact body has a flat contact surface or a curved contact surface.

7. The ophthalmic device of claim 1, wherein the ophthalmic device comprises a patient interface device configured to be fastened to the eye of a patient; and the optical correction element is securely or detachably connected to the patient interface device.

8. The ophthalmic device of claim 1, wherein the ophthalmic device comprises a patient interface device; the patient interface device has a cavity provided for holding liquid, and an opening, which opening is closed by the eye tissue in a state of the patient interface device in which it is fastened to the eye tissue.

9. The ophthalmic device of claim 1, further comprising a detection module configured to detect the optical correction element and control a setting of the scanning device depending on a detection of the optical correction element.

10. The ophthalmic device of claim 9, wherein the detection module is configured to detect the optical correction element by detecting at least one of: a type of correction element, a position of the correction element, optical properties of the correction element, a thickness of the correction element, or dimensions of the correction element.

11. The ophthalmic device of claim 9, wherein the detection module comprises at least one of: an optical sensor, a distance sensor, or an RFID sensor.

12. The ophthalmic device of claim 1, wherein the scanning device is configured to move the mirror about a pivot point lying on an optical axis of the optical focusing unit and on a surface of the movable mirror.

13. The ophthalmic device of claim 1, wherein the scanning device comprises a plurality of linear drives coupled to the movable mirror; and the ophthalmic device comprises a control module configured to control the linear drives to rotate the movable mirror about a pivot point lying on an optical axis of the optical focusing unit and on a surface of the movable mirror.

14. An ophthalmic device for treating eye tissue using laser pulses, comprising:
- a laser source configured to produce the laser pulses;
- an optical focusing unit configured to focus the laser pulses;
- a scanning device, with a movable mirror, arranged downstream from the optical focusing unit, and configured to deflect the laser pulses from the optical focusing unit in at least one deflection direction, whereby moving the mirror causes an image field curvature; and
- an optical correction element arranged downstream of the scanning device and configured to correct the image field curvature, by imaging, in a focused manner, the laser pulses deflected by the scanning device on an intended treatment area in the eye tissue,
- wherein the optical correction element comprises a lens configured to image, in the focused manner, the laser pulses deflected by the scanning device onto a focus with a reduced spot size.

15. An ophthalmic device for treating eye tissue using laser pulses, comprising:
- a laser source configured to produce the laser pulses;
- an optical focusing unit configured to focus the laser pulses;
- a scanning device, with a movable mirror, arranged downstream from the optical focusing unit, and configured to deflect the laser pulses from the optical focusing unit in at least one deflection direction, whereby moving the mirror causes an image field curvature; and
- an optical correction element arranged downstream of the scanning device and configured to correct the image field curvature, by imaging, in a focused manner, the laser pulses deflected by the scanning device on an intended treatment area in the eye tissue,
- wherein the optical correction element comprises a lens configured to image, in the focused manner, the laser pulses deflected by the scanning device onto a focus with defined spot quality, the defined spot quality comprising at least one of: size of a spot, shape of the spot, diameter of the spot across a projection direction, and length of the spot in the projection direction.

16. A device comprising:
- an optical focusing unit configured to focus laser pulses;
- a scanning device, with a movable mirror, arranged downstream from the optical focusing unit, and configured to deflect the laser pulses from the optical focusing unit in at least one deflection direction, whereby moving the mirror causes an image field curvature; and
- an optical correction element arranged downstream of the scanning device and configured to correct the image field curvature, by imaging, in a focused manner, the laser pulses deflected by the scanning device on an intended treatment area in the eye tissue,
- wherein the optical correction element is further configured to produce a defined displacement or enlargement of a focal length of the optical focusing unit.

* * * * *